United States Patent [19]

Specht et al.

[11] 4,241,611
[45] Dec. 30, 1980

[54] ULTRASONIC DIAGNOSTIC TRANSDUCER ASSEMBLY AND SYSTEM

[75] Inventors: Donald F. Specht, Los Altos; Julian Dow, Mountain View, both of Calif.

[73] Assignee: Smith Kline Instruments, Inc., Sunnyvale, Calif.

[21] Appl. No.: 16,782

[22] Filed: Mar. 2, 1979

[51] Int. Cl.³ .................................. G01N 29/00
[52] U.S. Cl. ............................. 73/626; 128/660; 367/103; 367/105
[58] Field of Search ........................ 128/660–663; 73/609, 612, 625–626; 367/103, 105

[56] References Cited

U.S. PATENT DOCUMENTS

| | | | |
|---|---|---|---|
| 4,011,750 | 3/1977 | Robinson | 73/602 |
| 4,012,952 | 3/1977 | Dory | 73/612 |
| 4,084,582 | 4/1978 | Nigam | 128/660 |
| 4,137,777 | 2/1979 | Haverl et al. | 128/660 |
| 4,138,895 | 2/1979 | Mezrich | 73/626 |

OTHER PUBLICATIONS

Kossoff, G. et al., "Octoson: A New Rapid Multi-Tx General Purpose Water Coupling Echoscope," Proc. Zd Eur. Cong. on UTS in Med. Munich Ger. 1975, pp. 90–95.
Alais, P. et al., "Acoustic Imaging with an Electronically Focussed & Scanned Array," Ibid, pp. 75–82.
Burckhardt, C. B. et al., "A Real-Time B Scanner with Improved Lateral Resolution," Ibid pp. 81–89.

Primary Examiner—Robert W. Michell
Assistant Examiner—Francis J. Jaworski
Attorney, Agent, or Firm—Flehr, Hohbach, Test

[57] ABSTRACT

An ultrasonic transducer assembly and system including a disc-shaped transducer element surrounded by ring-shaped transducer elements of different width to permit dynamic focusing and minimum phase cancellation. The elements are switched so that the output signals for various depths have a small dynamic range whereby the dynamic range of associated amplifiers is significantly reduced.

4 Claims, 6 Drawing Figures

ULTRASONIC DIAGNOSTIC TRANSDUCER ASSEMBLY AND SYSTEM

This invention relates generally to an ultrasonic diagnostic transducer assembly and system and more particularly to such a system incorporating an improved transducer.

Ultrasonic diagnostic apparatus is gaining wide acceptance because it can be used to image body organs without resort to ionizing radiation and with no known risk to the patient.

In such apparatus, a transducer is acoustically coupled to the body and is energized with pulses of ultrasonic energy so that the ultrasonic energy propagates through the body. When the pulse of ultrasonic energy strikes a boundary between two substances having different acoustic impedances, a portion of the energy is reflected, some of it returning as an echo to the transducer which also acts as a receiver. The remaining portion of the original energy is available to produce additional echoes from deeper interfaces. The return signals are appropriately processed with the time lapse between transmission and reception indicating the distance or depth of the interfaces. The processed signals can be recorded and/or displayed such as on a strip chart or cathode ray tube to show the relative positions of the interfaces in the body and display internal organs and the like.

Prior art systems have included single-element transducers and linear and annular arrays of transducers. Single-element transducers have been manually and mechanically scanned to analyze and diagnose sectors or regions of the body. Linear arrays have beams which can be electronically scanned and, with appropriate phasing networks, can be electronically focused at changing ranges in synchronism with the depth from which echoes are being received. This feature is usually called dynamic focusing. Annular phased arrays can be made to achieve dynamic focusing in both lateral dimensions, but generally must be scanned mechanically. Thin ring single element transducers are inherently focused optimally at all depths, but are not used extensively because their sensitivity is poor.

It is observed that in prior art systems employing a plurality of transducers, there is a necessity for multiple leads one to each of the transducer elements, multiple r-f amplifiers, multiple delay lines with wide dynamic range and complex processing circuitry to provide a display. Thus, prior art systems are generally relatively complex, expensive to manufacture, and require skilled technicians for their operation.

It is an object of the present invention to provide an improved ultrasonic diagnostic system which is simple and relatively inexpensive to manufacture.

It is another object of the present invention to provide an ultrasonic transducer assembly for such a system which includes a limited number of transducers, has high lateral resolution, and requires limited transmitted power while providing high sensitivity with small phase error.

The foregoing and other objects of the invention are achieved by an ultrasonic diagnostic system which includes a transducer including a plurality of concentric transducers adapted to transmit energy and selectively receive energy from different depths by selective connection of the transducers to associated apparatus.

The system includes a dishshaped ultrasonic transducer (typically a segment of a sphere) which is divided into a plurality of concentric annular transducer elements of which the innermost element may be either an annulus or a complete dish. One of the elements (typically the outermost) is used for transmitting a pulse of ultrasonic energy, and all of the elements (typically including the transmitting one) are used at various time intervals to receive the energy reflected from reflectors in the body under examination. All of the elements are used together to collect energy reflected from the deepest tissue ranges. At shorter ranges some of the elements are simply not used.

Thus the present invention combines in one transducer system the best features of the single-element bowl and the thin ring while overcoming the disadvantages inherent in each type without resorting to the complexity of an annular phased array or other two-dimensional phased array.

It is well known that for a given array aperture, the ring transducer produces the narrowest possible beam in both transmit and receive modes at all ranges. Its disadvantage is that a thin ring has poor sensitivity because of the relatively small area of its collecting surface. On the other hand, it is also known that the most efficient collector and most sensitive transducer is a spherical segment of maximum aperture with a center of curvature at the boundary which generates the echo. Maximum sensitivity is required only when receiving echo signals from maximum depth in the body. At somewhat closer ranges the signal strength of a thin ring is equivalent to that from the full bowl at maximum range. Consequently, by switching, the same electronic processing system can be used for both the bowl and thin rings. More than one thin ring may be desirable because the compromise between area of the transducer surface and phase cancellation across the surface varies with depth. Since for each depth range a single ring transducer provides the entire signal (with the exception of the use of all of the elements in parallel to form the full bowl at maximum depth), no complex signal processing circuitry is needed to combine signals from different elements. The high speed switching circuitry needed to selectively switch the one or more receiving elements is relatively simple compared with that used in phased array processing.

Fortunately, sensitivity is not an important issue on transmit because the power output is limited more by considerations of patient safety than by the capabilities of piezoelectric materials. Therefore, it is possible to use only a single ring of the transducer for transmit and achieve the well collimated beam pattern typical of ring transducers.

In the following description the matching and backing layers which would normally be used with the transducers are not shown. Furthermore the mounting of the transducer to operate is not shown. All of the foregoing is well known.

Figure 1:
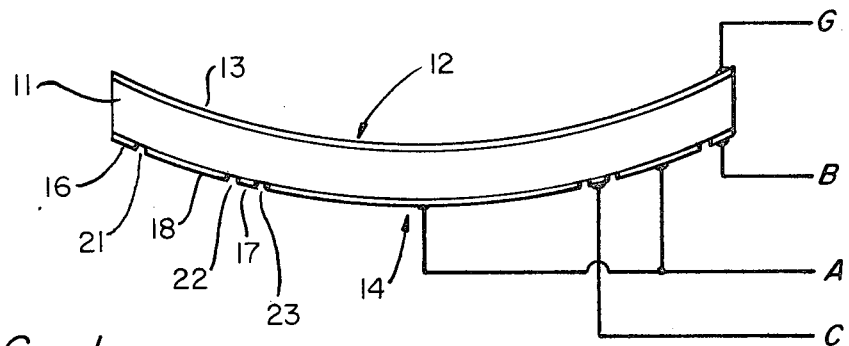
FIG. 1 is a sectional view of a transducer in accordance with the invention taken along the line 1—1 of FIG. 2.
Figure 2:
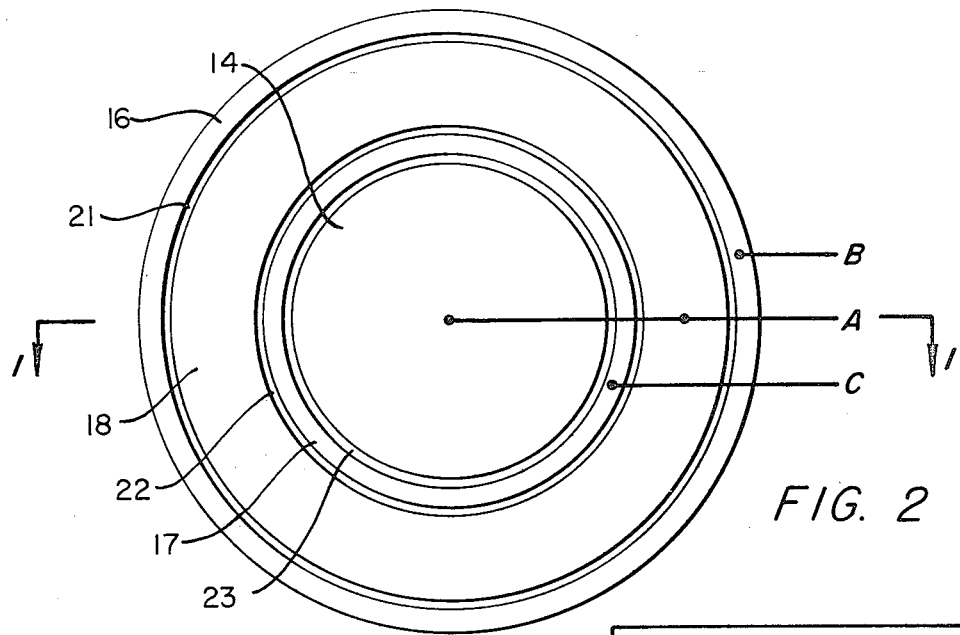
FIG. 2 is a rear view of the transducer of FIG. 1 showing the transducer elements.

Referring now to FIGS. 1 and 2, there is shown a multielement transducer in accordance with one embodiment of the invention. The transducer comprises a piezoelectric material such as a barium titanate, lead titanate, lead zirconate titanate, lead metaniobate, or other compounds which generates sound waves when electrically excited and generates electrical signals responsive to impinging sound waves. The transducer is preferably cupped to focus the ultrasonic energy along a line perpendicular to the face 12 and extending through the axis. The transducer 11 is provided with a conductive front surface 13 and a plurality of rear conducting surface elements designated generally by the reference numeral 14. As is well known, by applying a voltage between the conductors 13 and 14, and electric field is set up within the piezoelectric material. This field causes the material to expand and contract and thereby cause ultrasonic energy to be generated at the front surface 12.

In general, the curvature of the front surface 12 and any lens or impedance matching layer between the transducer and the patient will determine the focal length of the transducer. The amplitude of the energy applied will determine the amplitude of the emitted ultrasonic waves which travel away from the face of the transducer.

In operation, the transducer is pulsed with a pulse of high frequency energy and thereafter the transducer acts as a receiver whereby sonic energy reflected from interfaces or objects is received by the transducer. The received energy causes the transducer to deform and generate output voltages. By appropriate phasing or timing, the distance of the reflecting surfaces from the transducer can be determined.

In accordance with the present invention, the conductive surface 14 is divided into a plurality of annular rings to form a plurality of transducer elements. Optionally, the rings can be further decoupled by etching, scribing, or complete cutting of the rings (in which case the front surfaces 12 would have to be reconnected in some way). By choosing the surface area of the individual elements and selectively connecting the elements to a receiver, energy from different depths can be efficiently received. The required dynamic range of the associated amplifier is significantly reduced. The particular embodiment shown includes an outer annular ring 16, inner annular rings 17 and 18 formed by not depositing or removing the conductive material at the regions 21, 22 and 23, respectively. Suitable electrical connection is made to the rings 16, 17 and 18 and to the remaining portions of the conductive surface 14. The connecting leads are shown connected to the terminals A, B and C. The front surface is shown connected to the common or ground terminal G.

A typical transducer for operating to depths of 25 cm could have a diameter of 40 mm with the outer ring 16 having a width of approximately 1.85 mm, providing a surface area of 222 mm$^2$; the inner ring 17 having a width of approximately 0.8 mm and lying at an approximate radius of 10.6 mm to provide a surface area of 55 mm$^2$; In operation, a pulse would be applied to the outer ring whereby there is transmitted a pulse of approximately 3 cycles of 3.5 MHz ultrasonic energy. Thereafter, the transducers are switched so that transducer element 17 receives energy for a predetermined time to receive energy reflected from interfaces located within a predetermined range or depth, for example, zero to about 6 cm. This ring has a narrow width whereby the energy received from along the focal line is substantially in phase across the face of the transducer. Although it has a small collection area and low sensitivity, this is unimportant for the short ranges. Thereafter, the transducer is switched whereby the outer ring element 16 receives energy for the distance or depth range from about 6 cm to about 21 cm. This provides good response because of the additional surface area which receives energy. For this range a somewhat wider ring is usable since phase cancellation across the width of the transducer is less of a problem with greater range. Finally, at the depths beyond 21 cm, the total transducer array serves to receive energy, that is, the transducer elements connected to leads A, B and C are connected together to receive energy from the entire face of the transducer thereby providing maximum sensitivity.

Figure 3:
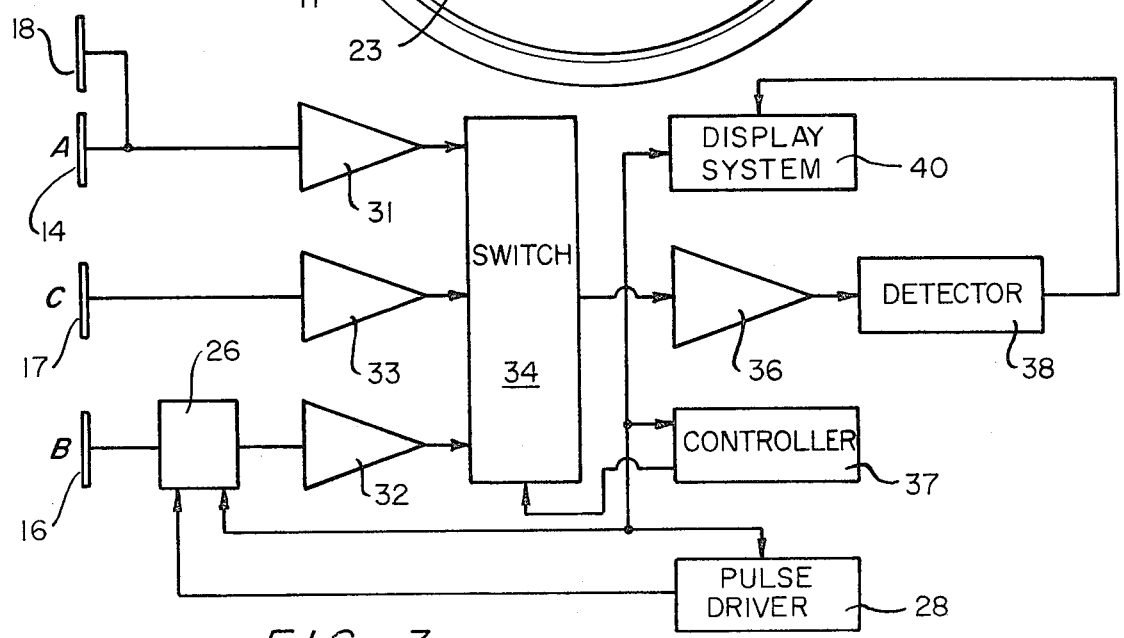
FIG. 3 is a schematic block diagram showing a electronic system for driving the transducer and receiving and processing energy from the transducer shown in FIGS. 1 and 2.

In FIG. 3 an electronic control system is shown connected to transducer leads A, B and C. Transducer lead B is shown connected to a transmit-receive switch 26. In the transmit mode transducer 16 is connected directly to the pulse driver (pulser) 28 by the T-R switch 26. By electronically controlling the switch 26 and activating the pulse driver 28, pulses of energy from the driver are applied through the transmit side of switch 26 to the transducer 16 which serves to emit a pulse of ultrasonic energy.

Each of the transducer elements is connected to an associated amplifier 31, 32 and 33, respectively. The amplifier 32 is connected to its transducer element through the transmit-receive switch 26 to receive the transducer lead B. The amplifiers 31, 32 and 33 are connected to a switch 34 which serves to control which amplifier is connected to the final amplification stage represented by amplifier 36. Switch 34 can be accomplished by any of a number of well known electronic means.

A controller 37 serves to control operation of the switches 26 and 34 whereby to provide appropriate switching. The controller, for example, may include a reference frequency source and suitable counters which provide outputs at predetermined counts to operate the individual switches 26 and 34. For example, the controller may control the switches in the sequence shown in FIG. 4.

Figure 4:
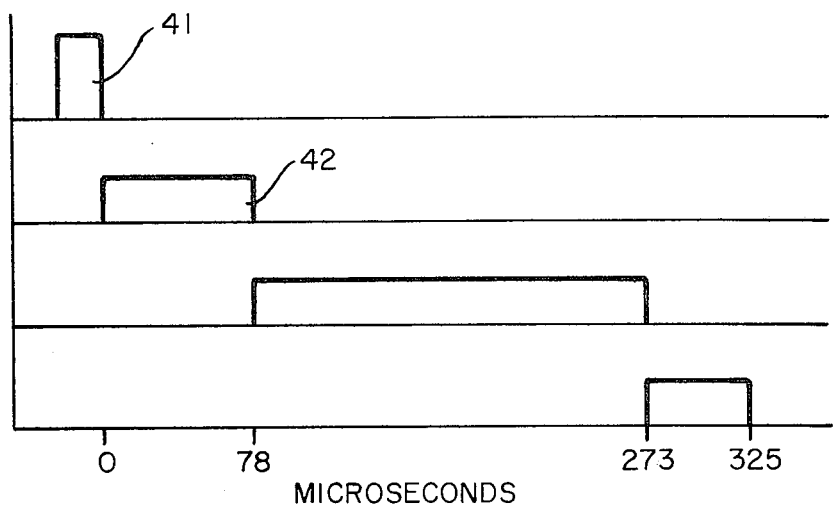
FIG. 4 is a timing diagram showing the receiving times for individual transducer elements shown in FIGS. 1-3.

Referring to FIG. 4, the controller first opens the switch 26 to provide a pulse 41 to the outer transducer element 16 connected to lead B whereby to energize the transducer and transmit ultrasonic energy. Thereafter, the controller controls the switch associated with the transducer lead C to receive signals from the transducer 17 amplified by amplifier 33 and apply them to the amplifier 36 for the period of time represented by the pulse 42. In this particular example, the switch is shown open for the period of time between time zero and 78 microseconds. This corresponds to a depth of approximately 6 cm. Thereafter, the controller serves to control the switch to connect the transducer line B to the amplifier 36 through amplifier 32 for the period of time between 78 microseconds and 273 microseconds, this corresponds to a depth of between 6 and 21 cm. Finally, the controller activates switch 34 to receive amplified signals from all three amplifiers 31, 32 and 33 and sum them in amplifier 36 for the period of time between 273 microseconds and 325 microseconds, thereby scanning the depth 21 to 25 cm. The switching is such that maximum energy is received by the transducer elements without excessive amounts of phase cancellation effects from scatterers on the main axis of the beam.

Output of the amplifier 36 is the signal output of the present transducer system. Typically this output would be applied to a detector 38 and then through suitable circuits to display system 40. The display system would include some means for mechanically scanning the transducer system described, pulsing the transducer at various rotational or translational positions, and displaying the echoes in a way to represent a two dimensional slice through the body or a three dimensional segment of the body. An elementary use of the transducer system would be in A mode or M mode where the transducer is not scanned and the signal is displayed as a function of time. On the other hand, the signals output from amplifier 36 may be digitized and subjected to digital signal processing prior to any form of display.

Figure 5:
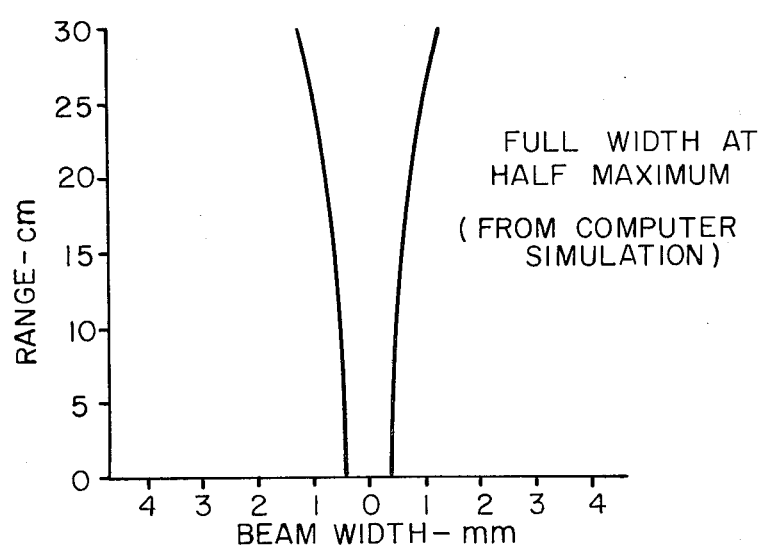
FIG. 5 is a plot showing effective round trip beam width as a function of range for a system employing transducer of the type shown and described.

The transducer system provides good focusing an illustrated in the diagram shown in FIG. 5 wherein the round-trip beamwidth is plotted as a function of range. The round-trip beamwidth is computed by multiplying the transmitted beam pattern by the composite received beam pattern. Beamwidth has been defined in various ways, but can be defined as the width of the product pattern from half amplitude on one side of the axis to half amplitude on the other side. It is seen that at 25 cm, the beamwidth so defined is only about 2½ mm. This is substantially improved resolution over fixed-focus systems since they are invariably focused at an intermediate range.

Figure 6:
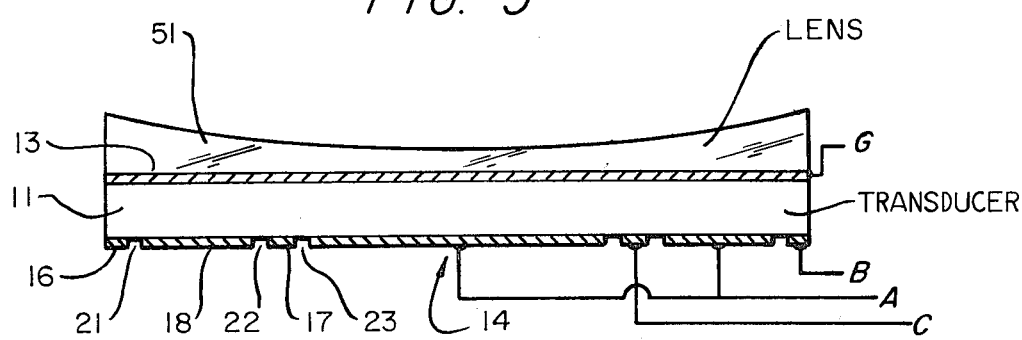
FIG. 6 shows another transducer assembly in accordance with the present invention.

In FIG. 6 there is shown another transducer assembly. Rather than shaping the transducer for focusing, the transducer is flat and an acoustic lens 51 is employed to focus the transducer. Since, except for the shape, the elements of the transducer are the same, identical reference numerals have been applied. The transducer would be connected to the associated electronic system in the same manner as the transducer previously described.

It is to be realized that transducers including more or fewer annular elements may be employed to provide good resolution and sensitivity at the various depths.

It is also apparent to one skilled in the art that one of the rings may be dedicated to transmit energy while the remainder of the rings may be used to receive. The transmit ring may also be a separate ring which can then be made of a different material which is more efficient as a transmitter than as a receiver. There has been provided an improved transducer system which is simple in construction, requires a minimum number of leads and associated circuits and is relatively simple to operate, but still retains the most important advantages of an annular phased array system; namely, dynamic focus, good lateral resolution in two dimensions, and maximum sensitivity.

What is claimed is:

1. An ultrasonic transducer assembly and system including means for transmitting ultrasonic energy into a body to be diagnosed, a disc-shaped transducer element, a first narrow ring-shaped transducer element closely spaced from and surrounding said disc, a second wider ring-shaped transducer element closely spaced from and surrounding said first ring-shaped transducer element, a third ring-shaped transducer element of intermediate width closely spaced from and surrounding said second transducer element, means for focusing said transducer elements, said focused transducer elements serving to receive transmitted ultrasonic energy reflected from interfaces in said body to be diagnosed and each providing an output electrical signal, means for sequentially receiving the electrical signals from said elements firstly from the first transducer element, secondly from said third transducer element and finally from all transducer elements to thereby provide a dynamically focused system which sequentially receives energy reflected at close range, intermediate range and distant range.

2. An ultrasonic transducer assembly and system as in claim 1 wherein at least one of said transducer elements additionally serves as said means for transmitting ultrasonic energy into said body.

3. An ultrasonic transducer assembly and system as in claim 1 wherein said means for focusing said transducer elements comprises dishing said elements.

4. An ultrasonic transducer assembly and system as in claim 1 wherein said means for focusing said transducer elements comprises a lens.

* * * * *